United States Patent [19]

Kotelnikov et al.

[11] 4,040,288
[45] Aug. 9, 1977

[54] DIFFERENTIAL MICROCALORIMETER

[76] Inventors: Grigory Vladimirovich Kotelnikov, Puschino, Mikroraion "G", 10, kv. 56; Gennady Petrovich Krylov, Puschino, Mikroraion AB, 9, kv. 50, both of Moskovskaya oblast, Serpukhovsky raion, U.S.S.R.

[21] Appl. No.: 664,267

[22] Filed: Mar. 5, 1976

[51] Int. Cl.² .......................................... G01N 25/00
[52] U.S. Cl. .................................................. 73/15 B
[58] Field of Search ........................... 73/15 B, 190 R

[56] References Cited

U.S. PATENT DOCUMENTS

| 3,263,484 | 8/1966 | Watson et al. | 73/15 |
|---|---|---|---|
| 3,473,382 | 10/1969 | Tabeling | 73/15 |
| 3,747,396 | 7/1973 | O'Neill | 73/15 |

Primary Examiner—Herbert Goldstein
Attorney, Agent, or Firm—Lackenbach, Lilling & Siegel

[57] ABSTRACT

A differential microcalorimeter comprises a means for programmed heating of cells which accommodate heating and thermosensitive elements, a means for measuring power output of a thermal process under study, an a-c voltage source and a temperature measuring circuit, as well as a variable resistor for adjusting the baseline. The outputs of the means for measuring power output of a thermal process under study and of the means for programmed heating of the cells are connected, via appropriate phase-sensitive switches, to the second terminals of the series connected heating elements having their interconnected first terminals connected, via an appropriate phase-sensitive switch, to a movable terminal of the variable resistor for adjusting the baseline.

8 Claims, 3 Drawing Figures

DIFFERENTIAL MICROCALORIMETER

The invention relates to apparatus for differential thermal analysis, and in particular, to a differential microcalorimeter.

Differential microcalorimeters are intended for measuring heat capacity and thermal effects in liquids and solids (in the form of films and powders) over a wide temperature range at various temperature scanning rates.

In addition, microcalorimeters may be used for studying, under isothermal conditions, thermal effects of various types at various points of the working temperature range, as well as in thermal analysis in organic and inorganic chemistry and chemistry of polymers, and also in biology for studying low-energy thermal processes.

Known in a art is the differential microcalorimeter, wherein first and second heating elements with their first terminals interconnected are accommodated in a working cell and in a reference cell, respectively. The cells accommodate first and second thermosensitive elements, respectively, wired in a temperature measuring circuit and electrically coupled with the inputs of a means for programmed heating of the cells and with those of a means for measuring the power of a thermal process under study. The outputs of those means are electrically coupled with the first and second heating elements with their second terminals connected to the terminals of a variable resistor for adjusting the baseline. Its a-c voltage source has a plurality of outputs of which a first output is connected to the control input of a first phase-sensitive switch, a second output is connected to the control input of a second phase-sensitive switch, and a third output is a unidirectional pulse output having a first terminal connected to the junction point of the first terminals of the heating elements and the other terminal connected, via members of a unidirectional pulse splitting circuit, to the second terminals of the heating elements.

In the above-described differential microcalorimeter, alternate connection of either the means for programmed heating of the cells or the means for measuring the power is effected by gating two pairs of diodes by the voltage fed from two respective transformer windings.

The diodes in the heating element circuits substantially impair the operation of the microcalorimeter. During the heating of the cells, the current flowing in the heating element varies within more than hundreds of times of its initial value, and the power supplied to the heating elements is partially consumed by the diodes in the circuit for programmed heating.

It should be noted that due to non-identical current-voltage characteristics of the diodes and various instabilities, a different amount of power is consumed in the diodes so that the means for measuring the power is effected and reacts in the same manner as to a thermal change to compensate this effect thus resulting in deviation and distorsion of the baseline of the differential microcalorimeter from the initial zero value.

The baseline is the line of temperature readings in the absence of the thermal process being measured.

The above-described instability of the baseline impairs the sensitivity of the apparatus and accuracy of measurements.

In addition, instability and non-identical operating conditions of the diodes inserted in the circuit of the means for measuring the power of the thermal process being controlled result in lower accuracy of conversion of the measured power value into a linear function of output current.

It is an object of the invention to provide a differential microcalorimeter having a high stability of the baseline over a wide range of programmed temperatures.

Still another important object of the invention is to provide a microcalorimeter having a greater sensitivity to changes in the thermal process under study and high accuracy in measuring the process energy.

A further object of the invention is to reduce zero drift of the baseline of a differential microcalorimeter.

With these and other objects in view, the invention comprises a differential microcalorimeter including first and second heating elements having their interconnected first terminals accommodated in a working cell and in a reference cell, respectively, which accommodate first and second thermosensitive elements, respectively, wired in a temperature measuring circuit and electrically coupled to inputs of a means for programmed heating of the cells and of a means for measuring the power of the thermal process under study. The outputs of these means are electrically coupled to the first and second heating elements having their second terminals connected to the terminals of a variable resistor for adjusting the baseline. An a-c voltage source has a plurality of outputs of which a first output is connected to the control input of a first phase-sensitive switch, a second output is connected to the control input of a second phase-sensitive switch and a third output comprises a unidirectional pulse output having one terminal connected to the junction point of the first termnals of the heating elements and a second terminal connected, via elements of a unidirectional pulse splitting circuit, to the second terminals of the heating elements. According to the invention, the output of the means for programmed heating of the cells is connected, via the first phase-sensitive switch, to the second terminals of the series connected heating elements which are also connected, via the second phase-sensitive switch, to the output of the means for measuring the power of the thermal process under study.

The elements of the unidirectional pulse splitting circuit of the microcalorimeter preferably comprise resistors.

The elements of the unidirectional pulse splitting circuit of the microcalorimeter may comprise inductance elements.

The a-c voltage source of the microcalorimeter is preferably provided with a fourth output comprising a unidirectional pulse output having terminals connected to the second terminals of the heating elements.

Furthermore, the microcalorimeter is preferably provided with a third phase-sensitive switch, and the a-c voltage source is further provided with a fifth output which is connected to the control input of the third phase-sensitive switch inserted between the movable terminal of the variable resistor and the junction point of the first terminals of the heating elements.

The a-c voltage source is preferably provided with a sixth output connected to the temperature measuring circuit.

The differential microcalorimeter according to the invention effects measurements of a thermal process over a wide temperature range.

The circuit according to the invention provides high accuracy and a sensitivity better than $10^{-5}$ W, as well as an improved stability of the baseline.

Still aother important advantage of the microcalorimeter according to the invention, as compared to conventional apparatus of the same general type, consists in the resulting simplified circuitry and elimination of the effect of parasitic electromotive forces induced with d-c power supply.

The apparatus according to the invention may be used for differential thermal analysis which permits obtaining exact and comprehesive calorimetric information on the sample being studied.

The invention will now be described with reference to specific embodiments thereof illustrated in the accompanying drawings, in which.

Figure 1:
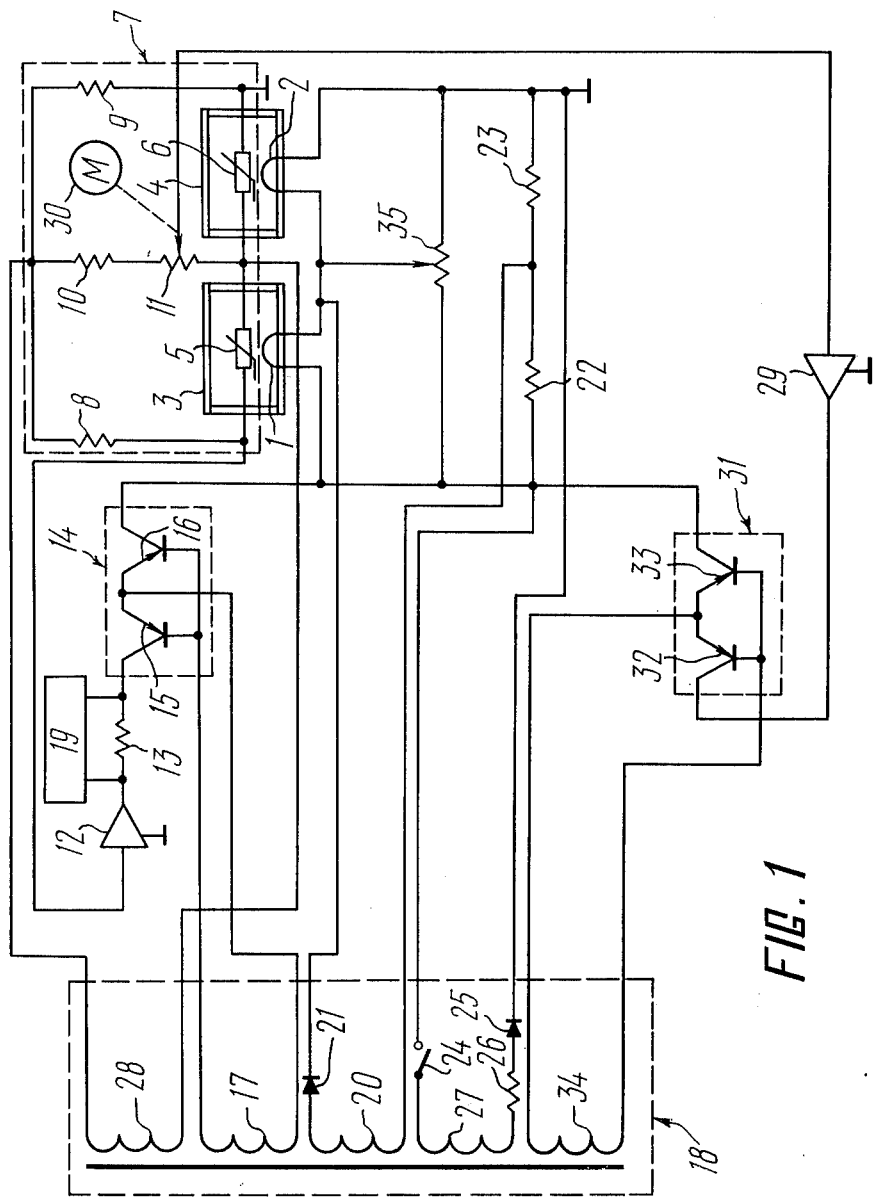
FIG. 1 shows a wiring diagram of the differential microcalorimeter according to the invention, with resistors used as elements of a unidirectional pulse splitting circuit.

The electric circuit of the differential microcalorimeter consists of a means for measuring the power of the thermal process under study, a means for programmed heating of the cells, a temperature measuring circuit and an a-c voltage source.

A first heating element 1 and a second heating element 2 having their first terminals interconnected are accommodated in a working cell 3 and in a reference cell 4, respectively.

The working cell 3 also accommodates a first thermosensitive element 5, and a second thermosensitive element 6 is accommodated in the reference cell 4.

The first thermosensitive element 5 and the second thermosensitive element 6 are inserted in a temperature measuring circuit 7 consisting of resistors 8, 9, 10 and a variable resistor 11.

The thermosensitive members 5 and 6 comprise resistance thermometers.

The means for measuring the power of the thermal process under study comprises an a-c amplifier built around a conventional circuit. The input of the amplifier 12 is connected to the measuring diagonal of a bridge circuit of the temperature measuring circuit 7. This bridge circuit consists of the resistors 8 and 9 and thermosensitive members 5 and 6.

The output of the amplifier 12 is connected, via a resistor 13, which detects an electric signal during the flow of the output current of the amplifier 12, and, via a phase-sensitive switch 14, to the heating elements 1 and 2 accommodated in the cells 3 and 4.

The phase-sensitive switch 14 consists of two transistors 15 and 16 connected to one of windings 17 of an a-c voltage source 18 and controlled by the voltage obtained from the winding 17.

A recording instrument 19 comprising a means for recording power output of the thermal process being controlled is connected to the resistor 13.

Another winding 20 of the a-c voltage source 18 is connected, via a diode 21 and resistors 22 and 23 of a unidirectional pulse splitting circuit, to the heating elements 1 and 2.

The second terminals of the heating elements 1 and 2 are connected, via a switch 24, a diode 25 and a resistor 26, to a winding 27 of the a-c voltage source 18.

The above-described measuring bridge circuit consisting of the resistors 8 and 9 and thermosensitive elements 5 and 6 is connected to a further winding 28 of the voltage source 18 which supplies this bridge circuit.

The rated values of the resistors 22 and 23 is by one order higher than the rated values of the resistance of the heating elements 1 and 2, and the rated values of the resistors 8 and 9 is much more higher than the rated values of the resistance of the thermosensitive elements 5 and 6 which provides for linear measurement of voltage across the elements 5 and 6 in relation to temperature.

The means for programmed heating of the cells comprises an a-c amplifier 29 built around a conventional circuit.

The input of the a-c amplifier 29 is connected to the measuring diagonal of another bridge circuit of the temperature measuring circuit 7 which is formed by the resistor 9, the thermosensitive element 6, the resistor 10 and the variable resistor 11 having its movable terminal coupled to an electric motor 30.

The output of the a-c amplifier 29 is connected, via a phase-sensitive switch 31, to the heating elements 1 and 2.

The phase-sensitive switch 31 consists of two transistors 32 and 33 connected to an isolated winding 34 of the voltage source 18 and controlled by the voltage obtained from the winding 34.

The junction point of the first terminals of the heating elements 1 and 2 is connected to the movable terminal of a variable resistor 35 having one of the other two terminals connected to the second terminal of the heating element 1 and the third terminal connected to the second terminal of the heating element 2.

Figure 2:
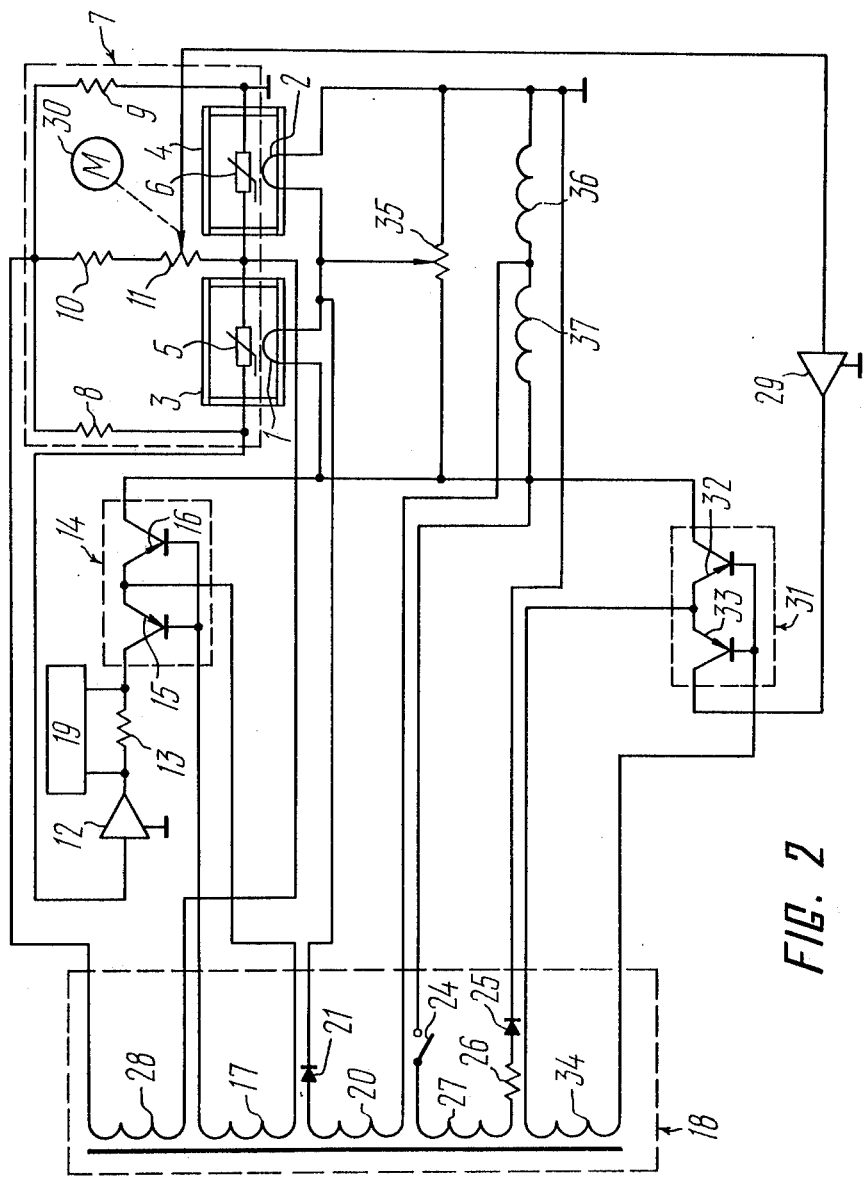
FIG. 2 shows another embodiment of the wiring diagram of the microcalorimeter according to the invention, with inductance elements of a unidirectional pulse splitting circuit.

FIG. 2 shows another embodiment of the differential microcalorimeter, wherein the members of the unidirectional pulse splitting circuit comprises inductance elements 36 and 37.

Figure 3:
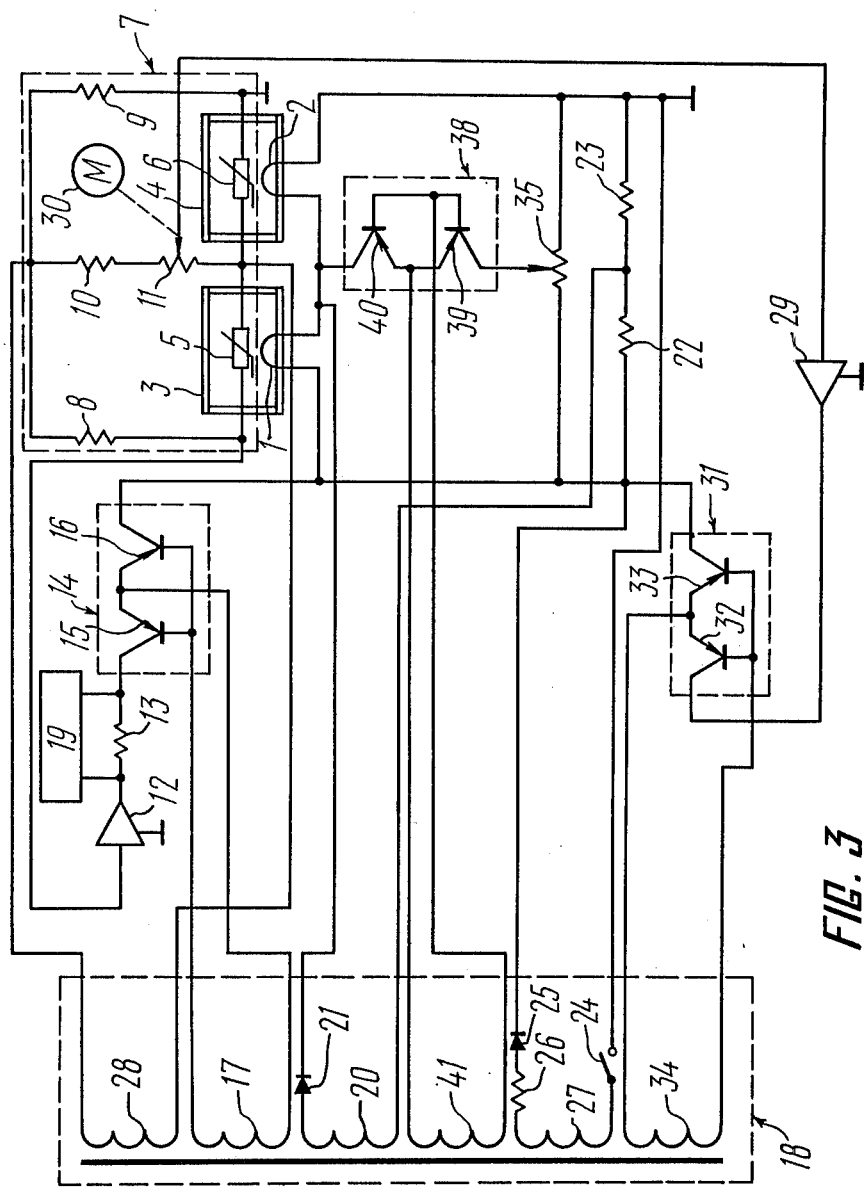
FIG. 3 shows a third embodiment of the wiring diagram of the differential microcalorimeter according to the invention, with a phase-sensitive switch inserted between the movable terminal of a variable resistor and the junction point of the first terminals of the heating elements.

A third embodiment of the differential microcalorimeter is shown in FIG. 3, which differs from the circuit shown in FIG. 1 in that the movable terminal of the variable resistor 35 is connected to the junction point of the first terminals of the heating elements 1 and 2 via a phase-sensitive switch 38 (FIG. 3). The switch consists of two transistors 39 and 40 connected to an isolated winding 41 of the voltage source 18 and controlled by the voltage obtained from the winding 41.

The differential microcalorimeter according to the invention functions in the following manner.

A specimen in a cup is placed in the working cell 3 (FIG. 1) and a reference specimen or an empty cup used to package the specimen is placed in the reference cell 4.

Then, using the means for programmed heating of the cells, the temperature in the cells is changed at a preset rate in accordance with the desired temperature scanning programme.

In the absence of a thermal process in the specimen under study, the measuring bridge circuit of the temperature measuring circuit 7 consisting of the resistors 8 and 9 and thermosensitive elements 5 and 6 is in the equilibrium state.

If a thermal process occurs in the studied specimen, the measuring bridge circuit becomes unbalanced, and an unbalance signal is fed to the input of the amplifier 12 wherefrom the amplified signal is fed, via the phase-sensitive switch 14, to the heating elements 1 and 2 of the cells 3 and 4.

An appropriate phase of the control voltage fed to the transistors 15 and 16 provides for feeding a signal from the output of the amplifier 12 to the heating elements 1 and 2 only during one of half-periods of the a-c voltage of the voltage source 18 in such a manner as to restore the equilibrium state of the bridge circuit.

During the same half-period, the voltage is also fed from the winding 20 of the voltage source 18 to the heating elements 1 and 2 via the resistors 22 and 23, with the currents flowing in opposition in the heating elements 1 and 2.

As a result, the output current of the amplifier 12 in one of the heating elements 1 and 2 is added to the current induced by the voltage from the winding 20, and in the other heating element this current is substracted from the current flowing as a result of the same voltage.

Thus, one of the cells 3 and 4 is cooled and the other cell is heated, and the equilibrium state of the measuring bridge circuit formed by the resistors 7 and 8 and the thermosensitive elements 5 and 6 is restored.

When the output current of the amplifier 12 flows in the resistor 13, a voltage proportional with the power output of the thermal process under study appears across this resistor. This voltage is recorded by the recording instrument 19.

A preset temperature scanning programme is performed by the means for programmed heating of the cells by varying the rotational speed of the electric motor 30 which may comprise a synchronous motor.

During rotation of the electric motor 30, the movable contact of the variable resistor 11 is displaced to unbalance the measuring bridge circuit of the temperature measuring circuit 7 formed by the resistors 10, 11 and 9 and the thermosensitive element 6. The unbalance signal from this bridge circuit is fed to the amplifier 29, and the output signal of this amplifier is fed, via the phase-sensitive switch 31, to the heating elements 1 and 2.

An appropriate phase of the control voltage fed to the transistors 32 and 33 from the winding 34 of the voltage source 18 provides for feeding a signal from the output of the amplifier 29 to the heating elements 1 and 2 only during than half-period of the a-c voltage of the voltage source 18 when there is no voltage at the output of the amplifier 12.

During this second half-period from the half-periods under consideration, a voltage is fed to the heating elements 1 and 2 from the output of the phase-sensitive switch 31 because during this half-period the voltage from the winding 20 cannot pass via the diode 21.

When current flows in the heating elements 1 and 2, the cells 3 and 4 are heated in accordance with a preset programme until the electric equilibrium in the measuring bridge circuit formed by the resistors 9, 10 and 11 and thermosensitive elements 5 and 6 is achieved.

Therefore, depending on the programme signal, an appropriate temperature scanning conditions in the cells 3 and 4 are obtained.

During the temperature scanning, an identical amount of power should be released in the heating elements 1 and 2. But this condition will not be fulfilled on account of different rated resistance values of the heating elements 1 and 2 due to the manufacturing tolerances.

Different amounts of power released in the heating elements 1 and 2 result in a slight inclination of the baseline of the differential microcalorimeter which makes the interpretation of test results complicated and hamper the handling of the data obtained.

In addition, the inclination of the baseline may result from non-identical area and blackness of the cells 3 and 4 which is manifested in unequal heat exchange of the cells 3 and 4 with the ambient medium.

In order to eliminate a possible slight inclination of the baseline, equal power release in the heating elements 1 and 2 having different rated values is obtained by using the variable resistor 35.

Furthermore, using the resistor 35, a constant ratio of power release in the heating elements 1 and 2 is obtained.

In case of large inclination of the baseline, an inadmissible non-linearity of conversion of the power of the thermal process under study into the function of the output current of the amplifier 12 occurs in compensating for this inclination due to a material difference in the shunting effect of the variable resistor 35 on the heating elements 1 and 2.

In order to eliminate this possible inconvenience during the compensation for a large inclination of the baseline, the circuit shown in FIG. 3 is used.

In this circuit, the movable terminal of the variable resistor 35 is connected to the junction point of the first terminals of the heating elements 1 and 2 via the phase-sensitive switch 38 controlled with the voltage from the winding 41 of the a-c voltage source 18.

The switch 38 is conductive only during that half-period of the a-c voltage when a signal from the output of the amplifier 29 is fed to the heating elements 1 and 2.

Thus, during the next half-period, the resistor 35 does not shunt the heating elements 1 and 2 so that during this half-period power output of the studied thermal process is converted into the linear function of the output current of the amplifier 12.

Thus, the inclination of the baseline can be adjusted over a wide range.

The electrical calibration voltage is fed from the winding 27 to the heating elements 1 and 2 upon actuation of the switch 24, and, since the circuit includes the diode 25, the electrical calibration is fed only during the first of the above-described half-periods, that is during that half-period within which a signal from the output of the amplifier 12 is fed to the heating elements 1 and 2.

The calibration voltage is in the form of unidirectional pulses, and the resistor 26 sets-up the power calibration value.

The calibration signal is fed to the heating elements 1 and 2 to be added to the voltage fed from the winding 20 of the voltage source 18 in one of the heating elements and to be subtracted from this voltage in the other heating element.

This results in a change in temperatures of the cells 3 and 4 and in unbalance of the measuring bridge circuit of the temperature measuring circuit 7 consisting of the resistors 8, 9 and thermosensitive elements 5 and 6. The means for measuring the power of the thermal process under study equlizes the temperatures in the cells 3 and 4 as described above, and the recording instrument 19 records the electric power input consumed for equalizing the temperatures in the cells 3 and 4.

The value of the power consumption thus obtained is used for establishment of the power scale of the differential microcalorimeter, that is the calibration of the apparatus is effected.

All time relations in the circuit of the differential microcalorimeter are provided for due to the fact that the windings 17, 20, 27, 28 and 34 are the windings of one and the same transformer the a-c voltage source 18.

The temperature measuring circuit 7 is supplied with a-c voltage fed from the winding 28 so as to dispense with modulators and eliminate parasitic electromotive forces.

The differential microcalorimeter according to the invention may be used as an apparatus for differential thermal analysis enabling comprehensive quantitative calorimetric information on the studied sample, and in particular, the data on changes in its energy and thermal capacity.

In the microcalorimeter according to the invention, a thermal process is measured over a wide range of temperature scanning (hundreds of degrees), while distorsions and instabilitites of the baseline are eliminated.

In addition, the apparatus according to the invention provides for an improved accuracy and high sensitivity, better than $10^{-5}W$.

The zero drift of the baseline is minimized thus providing for studies of multistage thermal processes occurring within a broad temperature interval.

The examples of such processes are vitrification, crystallization and melting.

Still another important advantage consists in a simplified circuit configuration due to elimination of complicated modulators, as well as elimination of the effect of parasitic electromotive forces induced with a d-c power supply.

An advantage of the differential microcalorimeter according to the invention also consists in the provision of electrical calibration of power scale by feeding calibration voltage to the same heating elements 1 and 2 of the cells 3 and 4 which are used in measurements.

This simulation of the thermal process in the cells 3 and 4 substantially facilitates the operation of the apparatus during calibration.

What is claimed is:

1. A differential microcalorimeter comprising: a first heating element having first and second terminals; a second heating element having first and second terminals, said first terminals of said heating elements being connected to each other; first and second thermosensitive elements; a working cell accommodating said first thermosensitive element and said first heating element; a reference cell accommodating said second heating element and said second thermosensitive element; a temperature measuring circuit incorporating said first and second thermosensitive elements, said temperature measuring circuit comprising resistors and said thermosensitive elements and arranged to form first and second measuring bridge circuits, said first bridge circuit comprising two parallel branches connected to each other to define a signal voltage input diagonal, each parallel branch including a resistor connected to one of said thermosensitive elements at a junction point, the two junction points of said two parallel branches defining a measuring diagonal of said first bridge, and said second bridge having a signal voltage input diagonal and a measuring diagonal; means for measuring the power of the thermal process under study having an input and an output; means for programmed heating of the cells having an input and an output; a first phase-sensitive switch having an input, an output and a control input; a second phase-sensitive switch having an input, an output and a control input, said input of said device for measuring the power of the thermal process under study being connected to the measuring diagonal of said first bridge circuit of said temperature measuring circuit, said input of said device for programmed heating of the cells being connected to said measuring diagonal of said second bridge circuit of said temperature measuring circuit, said output of said means for measuring the power of the thermal process under study being connected to said input of said first phase-sensitive switch; said output of said means for programmed heating being connected to said input of said second phase-sensitive switch, said outputs of said first and second phase-sensitive switches being connected to said heating elements; a variable resistor for adjusting the baseline having a first, movable terminal connected to said first terminals of said heating elements and two second terminals connected to said second terminals of said heating elements; an a-c voltage source having a plurality of outputs a first of which is connected to said control input of said first phase-sensitive switch, a second of said outputs of said a-c voltage source is connected to said control input of said second phase-sensitive switch, a third of said outputs of said a-c voltage cource comprising a unidirectional pulse output which consists of two terminals the first of which is connected to said first terminals of said heating elements and said second terminal is connected, via elements of a unidirectional pulse splitting circuit, to said second terminals of said heating elements.

2. A microcalorimeter according to claim 1, wherein said elements of the unidirectional pulse splitting circuit comprises resistors.

3. A microcalorimeter according to claim 1, wherein said elements of the unidirectional pulse splitting circuit comprise inductance elements.

4. A microcalorimeter according to claim 1, wherein said a-c voltage source is further provided with a fourth output which comprises a unidirectional pulse output having terminals connected to said secnd terminals of said heating elements.

5. A microcalorimeter according to claim 1, wherein there is further provided a third phase-sensitive switch, and said a-c voltage source is further provided with a fifth output connected to the control input of said third phase-sensitive switch which is inserted between said movable terminal of said variable resistor and said first terminals of said heating elements.

6. A microcalorimeter according to claim 1, wherein said a-c voltage source is further provided with a sixth output connected to said temperature measuring circuit.

7. A microcalorimeter according to claim 1, wherein said second bridge circuit comprises two parallel branches connected to each other to define said signal voltage input diagonal, one parallel branch including series-connected resistors one of which is a variable resistor, and the other parallel branch including a resistor connected to said second thermosensitive element at a junction point, said variable resistor having a movable contact which together with the last mentioned junction point define said measuring diagonal of said second bridge.

8. A differential microcalorimeter comprising: a first heating element having first and second terminals; a second heating element having first and second terminals, said first terminals of said heating elements being connected to each other; first and second thermosensitive elements; a working cell accommodating said first thermosensitive element and said first heating element; a reference cell accommodating said second heating element and said second thermosensitive element; a temperature measuring circuit incorporating said first and second thermosensitive elements, said temperature measuring circuit comprising resistors and said first and second thermosensitive elements which form first and second measuring bridge circuits, the first measuring bridge circuit comprising resistors and both of said thermosensitive elements, and the second measuring bridge circuit comprising resistors and one of said thermosenstive elements; means for measuring the power of the thermal process under study comprising said first measuring bridge circuit and an amplifier whose input is connected in the diagonal of said first measuring bridge circuit, the output of said amplifier being connected via a resistor to the input of said first phase-sensitive switch and said resistor serving as a source of signal proportional to the power being measured; means for programmed heating of the cells having an input, and an output; a first phase-sensitive switch having an input, an output and a control input, a second phase-sensitive switch having an input, an output and a control input, said input of said device for programmed heating of the cells being connected to said measuring diagonal of said second bridge circuit of said temperature measuring circuit, said output of said device for programmed heating of cells being connected to said input of said second phase-sensitive switch; said output of said means for programmed heating being connected to said input of said second phase-sensitive switch; said outputs of said first and second phase-sensitive switches being connected to said heating elements, the current fed to said heating elements from said amplifier ensuring said first measuring bridge and cells to restore the null; a variable resistor for adjusting the baseline having a first movable terminal connected to said first terminals of said first and second heating elements and two second terminals connected to said second terminals of said heating elements; an a-c voltage source having a plurality of outputs a first of which is connected to said control input of said first phase-sensitive switch, a second of said outputs of said a-c voltage source is connected to said control input of said second phase-sensitive switch, a third of said outputs of said a-c voltage source is an output of unidirectional pulses which has two terminals the first of which is connected to said first terminals of said heating elements and said second terminal is connected, via elements of a unidirectional pulse splitting circuit, to said second terminals of said heating elements.

* * * * *